United States Patent
Young et al.

(10) Patent No.: US 11,751,366 B1
(45) Date of Patent: Sep. 5, 2023

(54) HEAT DISSIPATION FOR HEAD-MOUNTABLE DEVICE

(71) Applicant: Apple Inc., Cupertino, CA (US)

(72) Inventors: Austin S. Young, Berkeley, CA (US); David A. Kalinowski, Redwood City, CA (US); Li Zhang, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 166 days.

(21) Appl. No.: 17/228,589

(22) Filed: Apr. 12, 2021

Related U.S. Application Data

(60) Provisional application No. 63/022,325, filed on May 8, 2020.

(51) Int. Cl.
*H05K 7/20* (2006.01)
*G02B 27/01* (2006.01)

(52) U.S. Cl.
CPC ..... *H05K 7/20963* (2013.01); *G02B 27/0172* (2013.01); *G02B 27/0176* (2013.01); *G02B 2027/0178* (2013.01)

(58) Field of Classification Search
CPC ............ G02B 27/0172; G02B 27/0176; G02B 2027/0178; H05K 7/20963
See application file for complete search history.

(56) References Cited

U.S. PATENT DOCUMENTS

| | | | |
|---|---|---|---|
| 9,545,030 B2 | 1/2017 | Nikkhoo et al. | |
| 9,684,172 B2 | 6/2017 | Border et al. | |
| 10,481,317 B2 | 11/2019 | Peroz et al. | |
| 10,888,037 B1 * | 1/2021 | Toleno | G02B 27/0006 |
| 2013/0258270 A1 * | 10/2013 | Cazalet | G02C 5/008 351/158 |
| 2016/0209659 A1 * | 7/2016 | Nikkhoo | G02C 5/18 |
| 2016/0246055 A1 * | 8/2016 | Border | G02B 27/0172 |
| 2018/0052501 A1 * | 2/2018 | Jones, Jr. | G02B 6/005 |

FOREIGN PATENT DOCUMENTS

JP 2020187188 A * 11/2020
WO WO 2021/109870 A1 6/2021

OTHER PUBLICATIONS

Translation of Probyn JP2020187188A.*

* cited by examiner

*Primary Examiner* — Jacob R Crum
(74) *Attorney, Agent, or Firm* — BAKERHOSTETLER

(57) ABSTRACT

A head-mountable device can provide passive cooling that utilizes surfaces of an optical assembly to allow heat to be managed in a manner that does not detrimentally impact the visual information displayed to the user. Lenses can be coated with a transparent and thermally conductive material, such as silver nanowire. Such a thermal layer can provide superior thermal conductivity, transmittance, flexibility, flat transmission, low cost, and angular color stability. The thermal layer can passively manage heat by increasing the surface area across which heat can be efficiently dissipated.

19 Claims, 2 Drawing Sheets

HEAT DISSIPATION FOR HEAD-MOUNTABLE DEVICE

CROSS-REFERENCE TO RELATED APPLICATION

This application claims the benefit of U.S. Provisional Application No. 63/022,325, entitled "HEAT DISSIPATION FOR HEAD-MOUNTABLE DEVICE," filed May 8, 2020, the entirety of which is incorporated herein by reference.

TECHNICAL FIELD

The present description relates generally to head-mountable devices, and, more particularly, to heat dissipation mechanisms for head-mountable devices, such as eyeglasses.

BACKGROUND

A head-mountable device can be worn by a user to display visual information within the field of view of the user. The head-mountable device can be used as a virtual reality (VR) system, an augmented reality (AR) system, and/or a mixed reality (MR) system. A user may observe outputs provided by the head-mountable device, such as visual information provided on a display. The display can optionally allow a user to observe an environment outside of the head-mountable device. Other outputs provided by the head-mountable device can include audio output and/or haptic feedback. A user may further interact with the head-mountable device by providing inputs for processing by one or more components of the head-mountable device. For example, the user can provide tactile inputs, voice commands, and other inputs while the device is mounted to the user's head.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

Figure 1:
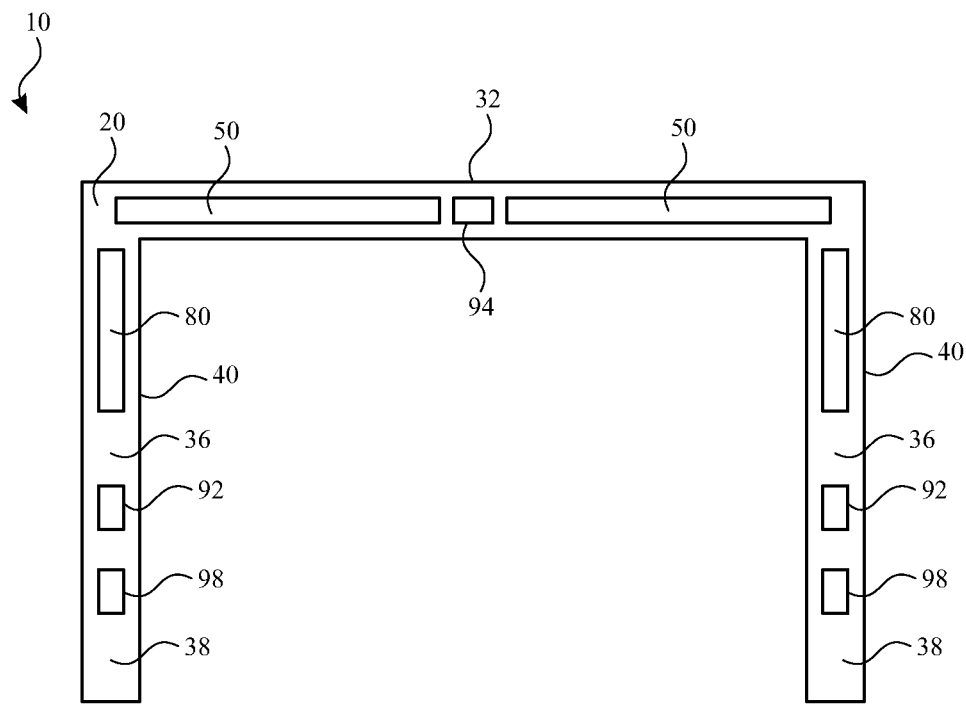
FIG. 1 illustrates a perspective view of a head-mountable device, according to some embodiments of the present disclosure.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details. In some instances, well-known structures and components are shown in block diagram form in order to avoid obscuring the concepts of the subject technology.

Head-mounted devices, such as head-mounted displays, headsets, visors, smartglasses, head-up display, etc., can perform a range of functions that are managed by the components (e.g., sensors, circuitry, and other hardware) included with the wearable device. Interactive systems including head-mounted devices can include multiple parts, such as a head-mounted device that supports an electronic device. The head-mounted device and/or the electronic device can provide the user with outputs such as audio and visual information. The head-mounted device and/or the electronic device can also receive inputs from a user.

Head-mounted devices are an attractive technology for providing an immersive user experience. For example, head-mounted devices are gaining increased popularity for providing VR, AR, and MR experiences for applications such as gaming, movies, or simulations for professional training, among other potential applications.

Maintaining efficient operation without unduly detracting from the user experience is a challenging task for head-mounted devices. Electronic components of a head-mounted device can generate heat during operation. Excessive heat for long durations of time can damage the components of the head-mounted device and cause discomfort to the user. The functionality of a head-mounted device may be limited by the thermal threshold that the user would be willing to accept.

At the same time, it can be desirable to provide a head-mountable device that is small and light-weight to maximize user comfort. Accordingly, the surface areas for dissipating heat can be limited by such design objectives. With limited surface areas on a slim form factor to dissipate heat, the head-mountable device faces thermal challenges that may restrict its functionality and features.

Systems of the present disclosure can manage heat without requiring actively controlled components. Passive cooling can utilize surfaces of an optical assembly to allow heat to be managed in a manner that does not detrimentally impact the visual information displayed to the user. Such surfaces can include the surfaces of the optical assembly, which provide to the user a view of a physical environment and/or other information. For example, an optical assembly can include one or more lenses that are coupled to a frame of the head-mountable device. Typically, lenses have the largest surface area for heat dissipation opportunity. However, the materials used for lenses is usually plastic or glasses, which have limited heat transfer capabilities, thereby leaving heat at the frame.

According to embodiments of the present disclosure, lenses can be coated with a transparent and thermally conductive material, such as silver nanowire. Silver nanowire can be used, rather than conventional ITO (Indium Tin Oxide), to provide superior thermal conductivity, transmittance, flexibility, flat transmission, low cost, and angular color stability. Such a thermally conductive coating need not be provided an electrically conductive connection between electrical components or an electrical pathway for actively managed resistive heating. Rather, the thermal layer can passively manage heat by increasing the surface area across which heat can be efficiently dissipated.

These and other embodiments are discussed below with reference to FIGS. 1-3. However, those skilled in the art will readily appreciate that the detailed description given herein with respect to these Figures is for explanatory purposes only and should not be construed as limiting.

According to some embodiments, for example as shown in FIG. 1, a head-mountable device 10 includes a frame 20 that is worn on a head with one or more arms 40. The frame 20 can be positioned in front of the eyes of a user to provide information within a field of view of the user. The frame 20 can provide nose pads or another feature to rest on a user's nose. The frame 20 further includes one or more optical modules 50 and a bridge 32 above the nose pads and connecting multiple optical modules 50.

The frame 20 and/or the arms 40 can serve to surround a peripheral region of the head-mountable device 10 as well as support any internal components in their assembled position. For example, the frame 20 and/or the arms 40 can enclose and support various internal components (including for example integrated circuit chips, processors, sensors, input/output devices, memory devices, and other circuitry) to provide computing and functional operations for the head-mountable device 10, as discussed further herein.

An optical module 50 can transmit light from a physical environment for viewing by the user. Such an optical module 50 can include optical properties, such lenses for vision correction based on incoming light from the physical environment. Additionally or alternatively, an optical module 50 can provide information as a display within a field of view of the user. Such information can be displayed based on operation of a display element 80 that projects light onto and/or communicates with one or more elements of the optical module 50. As shown in FIG. 1, the display element 80 can reside, at least partially, in one or more of the arms 40 and/or in the frame 20. For example, the display element 80 can reside, at least partially, within a cavity extending from the frame 20 and into the arm 40. Displayed information can be provided to the exclusion of a view of a physical environment or in addition to (e.g., overlaid with) a physical environment.

A physical environment refers to a physical world that people can sense and/or interact with without aid of electronic systems. Physical environments, such as a physical park, include physical articles, such as physical trees, physical buildings, and physical people. People can directly sense and/or interact with the physical environment, such as through sight, touch, hearing, taste, and smell.

In contrast, a computer-generated reality (CGR) environment refers to a wholly or partially simulated environment that people sense and/or interact with via an electronic system. In CGR, a subset of a person's physical motions, or representations thereof, are tracked, and, in response, one or more characteristics of one or more virtual objects simulated in the CGR environment are adjusted in a manner that comports with at least one law of physics. For example, a CGR system may detect a person's head turning and, in response, adjust graphical content and an acoustic field presented to the person in a manner similar to how such views and sounds would change in a physical environment. In some situations, (e.g., for accessibility reasons), adjustments to characteristic(s) of virtual object(s) in a CGR environment may be made in response to representations of physical motions (e.g., vocal commands).

A person may sense and/or interact with a CGR object using any one of their senses, including sight, sound, touch, taste, and smell. For example, a person may sense and/or interact with audio objects that create 3D or spatial audio environment that provides the perception of point audio sources in 3D space. In another example, audio objects may enable audio transparency, which selectively incorporates ambient sounds from the physical environment with or without computer-generated audio. In some CGR environments, a person may sense and/or interact only with audio objects.

Examples of CGR include virtual reality and mixed reality.

A virtual reality (VR) environment refers to a simulated environment that is designed to be based entirely on computer-generated sensory inputs for one or more senses. A VR environment comprises a plurality of virtual objects with which a person may sense and/or interact. For example, computer-generated imagery of trees, buildings, and avatars representing people are examples of virtual objects. A person may sense and/or interact with virtual objects in the VR environment through a simulation of the person's presence within the computer-generated environment, and/or through a simulation of a subset of the person's physical movements within the computer-generated environment.

In contrast to a VR environment, which is designed to be based entirely on computer-generated sensory inputs, a mixed reality (MR) environment refers to a simulated environment that is designed to incorporate sensory inputs from the physical environment, or a representation thereof, in addition to including computer-generated sensory inputs (e.g., virtual objects). On a virtuality continuum, a mixed reality environment is anywhere between, but not including, a wholly physical environment at one end and virtual reality environment at the other end.

In some MR environments, computer-generated sensory inputs may respond to changes in sensory inputs from the physical environment. Also, some electronic systems for presenting an MR environment may track location and/or orientation with respect to the physical environment to enable virtual objects to interact with real objects (that is, physical articles from the physical environment or representations thereof). For example, a system may account for movements so that a virtual tree appears stationery with respect to the physical ground.

Examples of mixed realities include augmented reality and augmented virtuality.

An augmented reality (AR) environment refers to a simulated environment in which one or more virtual objects are superimposed over a physical environment, or a representation thereof. For example, an electronic system for presenting an AR environment may have a transparent or translucent display through which a person may directly view the physical environment. The system may be configured to present virtual objects on the transparent or translucent display, so that a person, using the system, perceives the virtual objects superimposed over the physical environment. Alternatively, a system may have an opaque display and one or more imaging sensors that capture images or video of the physical environment, which are representations of the physical environment. The system composites the images or video with virtual objects, and presents the composition on the opaque display. A person, using the system, indirectly views the physical environment by way of the images or video of the physical environment, and perceives the virtual objects superimposed over the physical environment. As used herein, a video of the physical environment shown on an opaque display is called "pass-through video," meaning a system uses one or more image sensor(s) to capture images of the physical environment, and uses those images in presenting the AR environment on the opaque display. Further alternatively, a system may have a projection system that projects virtual objects into the physical environment, for example, as a hologram or on a physical surface, so that a person, using the system, perceives the virtual objects superimposed over the physical environment.

An augmented reality environment also refers to a simulated environment in which a representation of a physical environment is transformed by computer-generated sensory information. For example, in providing pass-through video, a system may transform one or more sensor images to impose a select perspective (e.g., viewpoint) different than the perspective captured by the imaging sensors. As another example, a representation of a physical environment may be transformed by graphically modifying (e.g., enlarging) portions thereof, such that the modified portion may be representative but not photorealistic versions of the originally captured images. As a further example, a representation of a physical environment may be transformed by graphically eliminating or obfuscating portions thereof.

An augmented virtuality (AV) environment refers to a simulated environment in which a virtual or computer generated environment incorporates one or more sensory inputs from the physical environment. The sensory inputs may be representations of one or more characteristics of the physical environment. For example, an AV park may have virtual trees and virtual buildings, but people with faces photorealistically reproduced from images taken of physical people. As another example, a virtual object may adopt a shape or color of a physical article imaged by one or more imaging sensors. As a further example, a virtual object may adopt shadows consistent with the position of the sun in the physical environment.

There are many different types of electronic systems that enable a person to sense and/or interact with various CGR environments. Examples include head-mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head-mountable system may have one or more speaker(s) and an integrated opaque display. Alternatively, a head-mountable system may be configured to accept an external opaque display (e.g., a smartphone). The head-mountable system may incorporate one or more imaging sensors to capture images or video of the physical environment, and/or one or more microphones to capture audio of the physical environment. Rather than an opaque display, a head-mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

Referring again to FIG. 1, a frame 20 can be supported on a user's head with the arms 40. The arms 40 can wrap or extend along opposing sides of a user's head, as with temple components 36. The arms 40 can further include earpieces 38 for wrapping around or otherwise engaging a user's ears. It will be appreciated that other configurations can be applied for securing the head-mountable device 10 to a user's head. For example, one or more bands, straps, belts, caps, hats, or other components can be used in addition to or in place of the illustrated components of the head-mountable device 10. By further example, an arm can extend about a user's head to both sides of the frame 20.

The frame 20 can be coupled to or integral (e.g., monolithic) with one or more of the arms 40, including the temple components 36 and/or the earpieces 38. For example, a continuous support structure including the frame 20 can support the optical modules 50 as well as the display elements 80. While at least a portion of the arms 40 can optionally move (e.g., the earpieces 38 pivot about a hinge and relative to the temple components 36) with respect to the frame 20, it will be understood that, in at least some embodiments, the frame 20 and/or the arms 40 can form a continuous structure that supports both the optical modules 50 as well as the display elements 80 to facilitate relative alignment of the optical modules 50 and their corresponding display element 80. As such, the arms 40 can refer to at least a portion of the support structure (e.g., temple components 36) that extends away from the portion of the frame 20 and that supports the optical modules 50.

In some embodiments, each of the optical modules 50 can include the display element 80 (e.g., a light projector) and a waveguide. The display element 80 can include any and all components for projecting light in the desired manner. For example, the display element 80 can include light sources, such as an RGB module, polarizers, beam splitters, collimators, lenses, and the like. The optical modules 50 can include a waveguide that allows internal reflections of received light, as well as one or more other optical components, such as corrective lenses.

Other electrical components can be positioned at various locations of the head-mountable device 10. For example, the head-mountable device 10 can include a sensor 94 for detecting one or more properties of a user, the head-mountable device 10, and/or an external environment. An example of a sensor 94 is illustrated in FIG. 1 as being positioned at the bridge 32 of the frame 20. It will be understood that the sensor 94 and/or other sensors can be positioned at other locations to effectively detect the target property.

By further example, the head-mountable device 10 can include a processor 92 for performing one or more processing functions and/or managing other electrical components. Other electrical components 98 can also be provided. While the processors 92 and the electrical components 98 are illustrated in the arms 40 of FIG. 1, it will be understood that these and/or other components can be positioned at any locations and provided with operative connections. Such components can generate heat while in use, and such heat can be directed outwardly toward the frame 20 and/or the arms 40 to be dissipated to an external environment. Such heat dissipation can be enhanced by providing thermally conductive surfaces at the optical modules 50, as described further herein.

Figure 2:
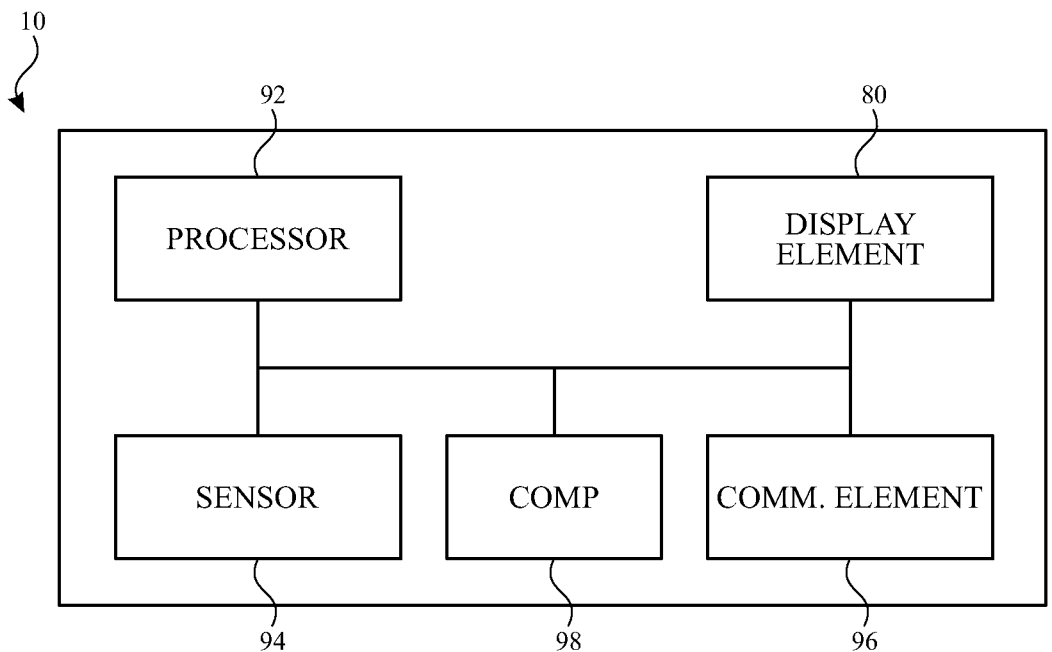
FIG. 2 illustrates a block diagram of a head-mountable device, in accordance with some embodiments of the present disclosure.

Referring now to FIG. 2, components of the head-mountable device can be provided and operatively connected to achieve the performance described herein. FIG. 2 shows a simplified block diagram of a head-mountable device 10 in accordance with one or more embodiments of the disclosure. It will be appreciated that components described herein, as well as other components, can be provided on either or both of a frame and/or one or more arms of the head-mountable device 10.

As shown in FIG. 2, the head-mountable device 10 can include a processor 92 with one or more processing units that include or are configured to access a memory having instructions stored thereon. The instructions or computer programs may be configured to perform one or more of the operations or functions described with respect to the head-mountable device 10. The processor 92 can be implemented as any electronic device capable of processing, receiving, or transmitting data or instructions. For example, the processor 92 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

The head-mountable device 10 can further include a display element 80 for displaying visual information for a user. The display element 80 can provide visual (e.g., image or video) output. The display element 80 can be or include an opaque, transparent, and/or translucent display. The display element 80 may have a transparent or translucent medium through which light representative of images is directed to a user's eyes. The display element 80 may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface. The head-mountable device 10 can include an optical subassembly configured to help optically adjust and correctly project the image-based content being displayed by the display element 80 for close up viewing. The optical subassembly can include one or more lenses, mirrors, or other optical devices, as discussed further herein.

The head-mountable device 10 can include one or more sensors 94. The sensor 94 can be or include a camera for capturing a view of an environment external to the head-mountable device 10. The camera can include an optical sensor, such as a photodiode or a photodiode array, a charge-coupled device (CCD) and/or a complementary metal-oxide-semiconductor (CMOS) device, a photovoltaic cell, a photo resistive component, a laser scanner, and the like. The camera may be configured to capture an image of a scene or subject located within a field of view of the camera.

Additionally or alternatively, the sensor 94 can be or include one or more environment sensors that are directed to an external environment. Such environment sensors can include any sensor that detects one or more conditions in an environment of the head-mountable device 10. For example, an environment sensor 160 can include an imaging device, a thermal sensor, a proximity sensor, a motion sensor, a humidity sensor, a chemical sensor, a light sensor, a magnetometer, a gyroscope, an accelerometer, a global positioning sensor, a tilt sensor, and/or a UV sensor. An environment sensor can be configured to sense substantially any type of characteristic such as, but not limited to, images, pressure, light, touch, force, temperature, position, motion, and so on.

Additionally or alternatively, the sensor 94 can be or include one or more user sensors for tracking features of the user wearing the head-mountable device 10. For example, a user sensor can perform facial feature detection, facial movement detection, facial recognition, eye tracking, user mood detection, user emotion detection, voice detection, etc. By further example, the user sensor can be a bio-sensor for tracking biometric characteristics, such as health and activity metrics.

The sensor 94 can include one or more eye sensors for tracking features of the user wearing the head-mountable device 100, including conditions of the user's eye (e.g., focal distance, pupil size, etc.). For example, such sensors can perform facial feature detection, facial movement detection, facial recognition, eye tracking, user mood detection, user emotion detection, voice detection, etc. For example, an eye sensor can optically capture a view of an eye (e.g., pupil) and determine a direction of a gaze of the user. Such eye tracking may be used to determine a location and/or direction of interest.

The head-mountable device 100 can include one or more other sensors. Such sensors can be configured to sense substantially any type of characteristic such as, but not limited to, images, pressure, light, touch, force, temperature, position, motion, and so on. For example, the sensor can be a photodetector, a temperature sensor, a light or optical sensor, an atmospheric pressure sensor, a humidity sensor, a magnet, a gyroscope, an accelerometer, a chemical sensor, an ozone sensor, a particulate count sensor, and so on.

The head-mountable device 10 can include a communication element 96 for communicating with one or more servers or other devices using any suitable communications protocol. For example, the communication element 96 can support Wi-Fi (e.g., a 802.11 protocol), Ethernet, Bluetooth, high frequency systems (e.g., 900 MHz, 2.4 GHz, and 5.6 GHz communication systems), infrared, TCP/IP (e.g., any of the protocols used in each of the TCP/IP layers), HTTP, BitTorrent, FTP, RTP, RTSP, SSH, any other communications protocol, or any combination thereof. The communication element 96 can also include an antenna for transmitting and receiving electromagnetic signals.

The head-mountable device 10 can include one or more other components for supporting operations thereof. For example, the head-mountable device 10 can include a battery (not shown), which can charge and/or power components of the head-mountable device 10. The battery can also charge and/or power components connected to the head-mountable device 10. By further example, the head-mountable device 10 can include an input/output component (not shown), which can include any suitable component for allowing a user to provide input and/or receive output. The input/output component can include, for example, one or more buttons, crowns, keys, dials, trackpads, microphones, speakers, haptic devices, and the like.

Figure 3:
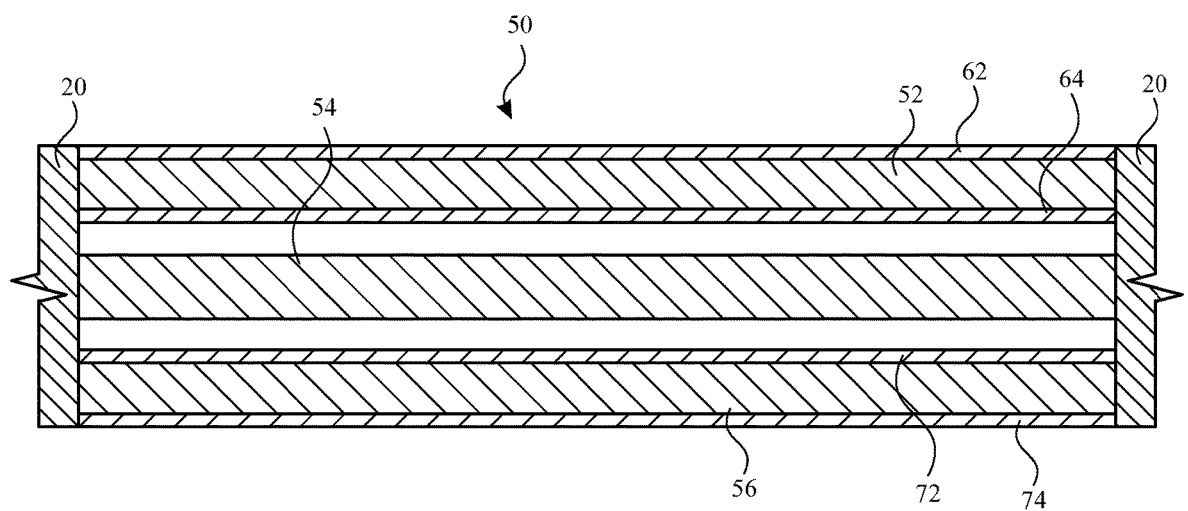
FIG. 3 illustrates a sectional view of a portion of a head-mountable device, including an optical assembly of the head-mountable device of FIG. 1, according to some embodiments of the present disclosure.

Referring now to FIG. 3, a head-mountable device can provide optical modules that provide enhanced heat management capabilities by maximizing surface areas for heat dissipation. Such decoupling can be achieved by utilizing an elastic bond with low stiffness to bond certain components together and absorb loads applied thereto. This allows the system to flex and deform without transferring stress to the waveguide.

As shown in FIG. 3, according to some embodiments, an optical module 50 can include a waveguide 54 between an inner lens 56 and an outer lens 52. The inner lens 56 can be positioned on a user side of the optical module 50 (e.g., facing toward the user when the head-mountable device is worn), and the outer lens 52 can be positioned on a world side of the optical module 50 (e.g., facing away from the user when the head-mountable device is worn).

The waveguide 54 can receive light from a display element, as discussed herein. The inner lens 56 can provide a window or other structure for transmitting light from the display element, through the inner lens 56, and to the waveguide 54. The waveguide 54 can include reflective surfaces. When the light enters the waveguide 54, it can strike a first surface with an angle of incidence greater than the critical angle above which total internal reflection occurs. The light may engage in total internal reflection and bounce between opposing surfaces until it reaches a viewing area. At the viewing area, the light can exit the waveguide 54 (e.g., at an angle less than the critical angle). While the waveguide 54 of FIG. 3 is shown as generally rectilinear, it will be understood that a variety of shapes and sizes can be provided to achieve the results discussed herein.

The inner lens 56 can apply optical effects to light transmitted from the waveguide 54 and to the user. For example, the inner lens 56 can be a negative or diverging lens. A given beam of light from the waveguide 54, after passing through the inner lens 56, can appear to emanate from a particular point beyond the inner lens 56 and/or the optical module 50 (e.g., from the external environment).

The outer lens 52 can also apply optical effects to light transmitted from an external environment and to the user. It will be recognized that, where the light from the waveguide 54 is superimposed on a view of an external environment, the inner lens 56 can apply an effect to both light from the waveguide 54 and the light from the external environment. While the effect of the inner lens 56 on the light from the waveguide 54 can be desirable, it can also be desirable to deliver light from the external environment with no net optical effect or with a different optical effect than would be provided by the inner lens 56 alone. As such, the outer lens 52 can apply an optical effect that negates, offsets, complements, or otherwise alters the effect of the inner lens 56 on incoming light from the external environment. For example, the outer lens 52 can be a positive or converging lens. A given beam of light from the external environment can pass through the outer lens 52 and receive a first optical effect. The same beam of light can further pass through the waveguide 54 and the inner lens 56 to arrive at the eye of the user with the intended optical effect.

It will be understood that the components of the optical module 50 can provide vision correction to incoming light as appropriate for a given user, for example, with the outer lens 52 and/or the inner lens 56. Such correction can be spherical, aspheric, atoric, cylindrical, single vision, multifocal, progressive, and/or adjustable. It will be understood that the components of the optical module 50 can include other optical components as required to produce a desired optical effect. For example, the outer lens 52, the waveguide 54, the inner lens 56, and/or another optical component can include one or more diffusers, filters, polarizers, prisms, beam splitters, diffraction gratings, mirrors, and/or windows. Such components can be positioned at any location adjacent to, within, or outside of the other components of the optical module 50.

To provide the desired optical properties, the inner lens 56 and/or the outer lens 52 can be of a material that both transmits light and is shapeable (e.g., to provide optical effects). Examples of such materials include plastic (e.g., polycarbonate) and glass. However, such materials generally have low thermal conductivity. As such, despite providing substantial surface area, the inner lens 56 and/or the outer lens 52 do not effectively dissipate heat generated at other locations of the head-mountable device.

As further shown in FIG. 3, one or more thermal layers can be provided on one or more of the lenses to draw heat away from the frame and dissipate the heat. The outer lens 52 can have, on an outer surface thereof, a thermal layer 62 that faces towards an external environment. Additionally or alternatively, the outer lens 52 can have, on an inner surface thereof, a thermal layer 64 that faces toward the waveguide 54. The thermal layers 62 and/or 64 can extend from one or more portions of the frame 20 and across a portion or an entirety of a side of the outer lens 52.

The inner lens 56 can have, on an outer surface thereof, a thermal layer 74 that faces towards the user. Additionally or alternatively, the inner lens 56 can have, on an inner surface thereof, a thermal layer 72 that faces toward the waveguide 54. The thermal layers 72 and/or 74 can extend from one or more portions of the frame 20 and across a portion or an entirety of a side of the inner lens 56.

While the outer lens 52 and the inner lens 56 are in thermal contact with the frame 20 and provide surface areas, the outer lens 52 and the inner lens 56 may include materials that provide poor and inefficient heat conduction. For example, lenses are conventionally made of materials that facilitate fabrication to provide the desired optical properties (e.g., vision correction). Examples of such materials include plastic (e.g., polycarbonate) and glass. These materials generally have thermal conductivity properties of less than 1 $W \cdot m^{-1} \cdot K^{-1}$. For example, polycarbonate has a thermal conductivity of 0.19-0.22 $W \cdot m^{-1} \cdot K^{-1}$, and ordinary glass has a thermal conductivity of 0.8 $W \cdot m^{-1} \cdot K^{-1}$. Accordingly, the outer lens 52 and the inner lens 56 do not dissipate notable amounts of heat despite the large surface areas thereof.

In contrast, the thermal layers 62, 64, 72, and/or 74 can have high thermal conductivity. In some embodiments, the thermal layers can include a material having thermal conductivity properties of greater than 10, 50, 100, 150, 200, 250, 300, 400, or 500 $W \cdot m^{-1} \cdot K^{-1}$. In some embodiments, the thermal layers can include a material including a metal, such as silver. For example, silver has a thermal conductivity of 406.0 $W \cdot m^{-1} \cdot K^{-1}$. As such, the thermal conductivity of the thermal layers can be greater than 10, 100, or 1,000 times the thermal conductivity of the corresponding lens.

The thermal layers 62, 64, 72, and/or 74 can be formed as small strands (e.g., "nanowires") that extend across the corresponding lens. As used herein, "nanowire" means a structure formed by a length a material having a width (e.g., measured across the length) that is less than 1 µm. For example, nanowires can have widths of less than 1 µm, 500 nm, 400 nm, 300 nm, 200 nm, 100 nm, 50 nm, 25 nm, or 10 nm. Each nanowire can extend along a length that is significantly longer than its width. The various nanowires can be provided in any arrangement relative to each other, including arrangements in which the nanowires cross, intersect, and/or overlap each other. The nanowires can be provided as a film and/or deposited directly onto the corresponding lens surface. A base material can optionally be provided to support the nanowires.

Within any given region of the lens surface, the nanowires can be arranged to cover only a portion of the total surface area. For example, the nanowires can be distributed to provide openings between adjacent nanowires, such that the openings leave the underlying lens surfaces exposed (e.g., uncovered by nanowires). Such openings can be large relative to the width of the nanowires. For example, the openings can be greater than 100 nm, 200 nm, 500 nm, 1 µm, or 2 µm. Accordingly, the total surface area that is exposed can be significantly greater than the total surface area that is covered. For example, the proportion of coverage can be less than 10%, and the proportion of exposure can be greater than 90%. Such exposure maintains significant transmission of light (e.g., transparency) through the thermal layers while simultaneously providing high thermal conductivity.

The thermal layers 62 and 74 that face away from the waveguide 54 (e.g., towards an external environment and/or the user) can facilitate dissipation of heat away from the frame 20 and away from the head-mountable device. For example, by providing heat dissipation along the thermal layers 62 and 74, the head-mountable device can have a significantly increased total surface area that facilitates heat dissipation.

The thermal layers 64 and 72 that face towards the waveguide 54 can facilitate dissipation of heat into a chamber containing the waveguide 54. For example, the waveguide 54 can be positioned within a chamber that is enclosed and/or sealed to minimize ingress of moisture therein. Where moisture has entered into the chamber, the moisture may condense on surfaces. Heat dissipated by the thermal layers 64 and 72 can increase a temperature within the chamber to evaporate the moisture and improve optical properties through the chamber.

It will be understood that the density, width, length, and/or number of nanowires can be constant across a given surface (e.g., between opposing sides of the frame 20). Additionally or alternatively, one or more of these properties can vary across a given surface. For example, the density, width, length, and/or number of nanowires can be greater at a region that is closer to the frame 20 to maximize the effect of drawing heat away from the frame 20. At other locations (e.g., at a central region of a lens), the density, width, length, and/or number of nanowires can be relatively smaller, optionally including a region having no nanowires.

It will be appreciated that the thermal layers described herein can provide dissipation of heat passively. For example, heat from the frame 20 (e.g., from components within the frame 20 or thermally connected thereto) can be drawn into the thermal layers without active controls.

Additionally or alternatively, the thermal layers can be arranged to provide operative, electrical, and/or communication connections between components. For example, the thermal layers can conduct electricity to provide communication between components. By further example, the thermal layers can be used to provide power to components, such as micro-LEDs, electronic tinting components, and/or guest host displays.

Additionally or alternatively one or more thermal layers can include other mechanisms for distributing heat. For example, one or more of the thermal layers can include or be accompanied by an ultra-thin vapor chamber (UTVC), which utilizes internal two-phase evaporation and condensation to passively transfer heat. A UTVC can facilitate heat transfer without any moving components. For example, a UTVC can include a liquid in a chamber that has the ability to absorb heat, vaporize into a gas, and transport the heat to cooler regions within a sealed chamber (e.g., to other portions extending across the waveguide 54). When the vapor releases its heat, it condenses back to a liquid and returns to its source. The source can include the source of generated heat. The path of the vapor and liquid can be achieved without requiring pumps or other moving parts.

Accordingly, embodiments of the present disclosure provide a head-mountable device with passive cooling that utilizes surfaces of an optical assembly to allow heat to be managed in a manner that does not detrimentally impact the visual information displayed to the user. Lenses can be coated with a transparent and thermally conductive material, such as silver nanowire. Such a thermal layer can provide superior thermal conductivity, transmittance, flexibility, flat transmission, low cost, and angular color stability. The thermal layer can passively manage heat by increasing the surface area across which heat can be efficiently dissipated.

Various examples of aspects of the disclosure are described below as clauses for convenience. These are provided as examples, and do not limit the subject technology.

Clause A: a head-mountable device comprising: a frame; and an optical module coupled to the frame, the optical module comprising: a waveguide; a display element configured to project light onto the waveguide; a lens positioned on a side of the waveguide; and a thermal layer on the lens, the thermal layer comprising silver nanowires for conducting heat from the frame across an outer surface of the lens.

Clause B: a head-mountable device comprising: a waveguide; an inner lens positioned on a first side of the waveguide; and an outer lens positioned on a second side of the waveguide, the inner lens and the outer lens each comprising a first material; and thermal layers on the inner lens and the outer lens, the thermal layers comprising a second material that conducts heat more efficiently than the first material.

Clause C: a head-mountable device comprising: a frame; arms extending from opposite sides of the frame; electrical components in each of the arms; an optical module for providing a view to an external environment, the optical module being supported by the frame, being thermally coupled to the electrical components, and having an thermal layer of a conductive material having a thermal conductivity of greater than 100 $W \cdot m^{-1} \cdot k^{-1}$.

One or more of the above clauses can include one or more of the features described below. It is noted that any of the following clauses may be combined in any combination with each other, and placed into a respective independent clause, e.g., Clause A, B, or C.

Clause 1: the lens is a first lens; the head-mountable device further comprises a second lens; and the waveguide is positioned between the first lens and the second lens.

Clause 2: the thermal layer is a first thermal layer on a first side of the first lens, the head-mountable device further comprising: a second thermal layer on a second side of the first lens; a third thermal layer on a first side of the second lens; and a fourth thermal layer on a second side of the second lens.

Clause 3: an arm extending away from the frame, wherein the display element is within the arm.

Clause 4: the lens has a thermal conductivity that is less than 1 $W \cdot m^{-1} \cdot k^{-1}$.

Clause 5: the optical module is a first optical module; and the head-mountable device further comprises a second optical module coupled to the frame.

Clause 6: the first material has a first thermal conductivity; and the second material has a second thermal conductivity that is at least 100 times greater than the first thermal conductivity.

Clause 7: the first thermal conductivity is less than 1 $W \cdot m^{-1} \cdot k^{-1}$; and the second thermal conductivity is greater than 400 $W \cdot m^{-1} \cdot k^{-1}$.

Clause 8: a frame; an arm extending away from the frame; and a display element within the arm and configured to project light onto the waveguide.

Clause 9: the thermal layers comprising: a first thermal layer on an inner side of the inner lens; a second thermal layer on an outer side of the inner lens; a third thermal layer on an inner side of the outer lens; and a fourth thermal layer on an outer side of the outer lens.

Clause 10: the optical module comprises: a first lens; a second lens; and a waveguide positioned between the first lens and the second lens.

Clause 11: a display element within one of the arms and configured to project light onto the waveguide.

Clause 12: the first lens and the second lens each has a thermal conductivity that is less than $1\ \text{W·m}^{-1}\text{·k}^{-1}$.

Clause 13: the thermal layer has a first thermal conductivity; and the first lens and the second lens each has a second thermal conductivity that is at least 100 times greater than the first thermal conductivity.

Clause 14: the conductive material has a thermal conductivity of greater than $400\ \text{W·m}^{-1}\text{·k}^{-1}$.

Clause 15: the conductive material is silver forming nanowires of the thermal layer As described above, one aspect of the present technology may include the gathering and use of data available from various sources. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A head-mountable device comprising:
    a frame; and
    an optical module coupled to the frame, the optical module comprising:
        a waveguide;
        a display element configured to project light onto the waveguide;
        a lens positioned on a side of the waveguide;
        a first thermal layer on a first side of the lens facing the waveguide and comprising silver nanowires, the first thermal layer being separated from the lens by a gap; and
        a second thermal layer on a second side of the lens, the second thermal layer defining an outermost end of the optical module and comprising silver nanowires for conducting heat from the frame across an outer surface of the lens.

2. The head-mountable device of claim 1, wherein:
    the lens is a first lens;
    the head-mountable device further comprises a second lens; and
    the waveguide is positioned between the first lens and the second lens.

3. The head-mountable device of claim 2, the head-mountable device further comprising:
    a third thermal layer on a first side of the second lens; and
    a fourth thermal layer on a second side of the second lens.

4. The head-mountable device of claim 1, further comprising an arm extending away from the frame, wherein the display element is within the arm.

5. The head-mountable device of claim 1, wherein the lens has a thermal conductivity that is less than $1 \ W \cdot m^{-1} \cdot K^{-1}$.

6. The head-mountable device of claim 1, wherein:
the optical module is a first optical module; and
the head-mountable device further comprises a second optical module coupled to the frame.

7. An optical module for a head-mountable device, the optical module comprising:
a waveguide;
an inner lens separated from a first side of the waveguide by a first gap;
an outer lens separated from a second side of the waveguide by a second gap, the inner lens and the outer lens each comprising a first material;
a first thermal layer on an inner side of the inner lens and defining an innermost end of the optical module; and
a second thermal layer on an outer side of the outer lens and defining an outermost end of the optical module, the first and second thermal layers comprising a second material that conducts heat more efficiently than the first material.

8. The optical module of claim 7, wherein:
the first material has a first thermal conductivity; and
the second material has a second thermal conductivity that is at least 100 times greater than the first thermal conductivity.

9. The optical module of claim 8, wherein:
the first thermal conductivity is less than 1 $W \cdot m^{-1} \cdot K^{-1}$; and
the second thermal conductivity is greater than 400 $W \cdot m^{-1} \cdot K^{-1}$.

10. The optical module of claim 7, further comprising:
a frame;
an arm extending away from the frame; and
a display element within the arm and configured to project light onto the waveguide.

11. The optical module of claim 7, wherein the second material is silver forming nanowires of the first and second thermal layers.

12. The optical module of claim 7, further comprising:
a third thermal layer on an outer side of the inner lens; and
a fourth thermal layer on an inner side of the outer lens.

13. A head-mountable device comprising:
a frame;
arms extending from opposite sides of the frame;
electrical components in each of the arms; and
an optical module for providing a view to an external environment, the optical module being supported by the frame, being thermally coupled to the electrical components, and comprising:
a waveguide;
an inner lens separated from a first side of the waveguide by a first gap;
an outer lens separated from a second side of the waveguide by a second gap, the inner lens and the outer lens each comprising a first material;
a first thermal layer on an inner side of the inner lens and defining an innermost end of the optical module; and
a second thermal layer on an outer side of the outer lens and defining an outermost end of the optical module, the first and second thermal layers comprising a second material that conducts heat more efficiently than the first material, the first and second thermal layers comprising a conductive material having a thermal conductivity of greater than 100 $W \cdot m^{-1} \cdot K^{-1}$.

14. The head-mountable device of claim 13, further comprising a display element within one of the arms and configured to project light onto the waveguide.

15. The head-mountable device of claim 13, the head-mountable device further comprising:
a third thermal layer on an inner side of the outer lens; and
a fourth thermal layer on an inner side of the outer lens.

16. The head-mountable device of claim 13, wherein the inner lens and the outer lens each has a thermal conductivity that is less than 1 $W \cdot m^{-1} \cdot K^{-1}$.

17. The head-mountable device of claim 13, wherein:
each of the first and second thermal layers has a first thermal conductivity; and
the inner lens and the outer lens each has a second thermal conductivity, wherein the first thermal conductivity is at least 100 times greater than the second thermal conductivity.

18. The head-mountable device of claim 13, wherein the conductive material has a thermal conductivity of greater than 400 $W \cdot m^{-1} \cdot K^{-1}$.

19. The head-mountable device of claim 13, wherein the conductive material is silver forming nanowires.

* * * * *

UNITED STATES PATENT AND TRADEMARK OFFICE
CERTIFICATE OF CORRECTION

| | | |
|---|---|---|
| PATENT NO. | : 11,751,366 B1 | Page 1 of 1 |
| APPLICATION NO. | : 17/228589 | |
| DATED | : September 5, 2023 | |
| INVENTOR(S) | : Austin S. Young et al. | |

It is certified that error appears in the above-identified patent and that said Letters Patent is hereby corrected as shown below:

In the Claims

Column 17, Lines 28-29 (Claim 9):
"400 W·m$^-_1$•K$^{-1}$" should read:
--400 W·m$^{-1}$•K$^{-1}$--

Signed and Sealed this
Second Day of January, 2024

Katherine Kelly Vidal
*Director of the United States Patent and Trademark Office*